United States Patent [19]
Iwakuma et al.

[11] Patent Number: 4,948,810
[45] Date of Patent: Aug. 14, 1990

[54] PHENOXYACETIC ACID DERIVATIVES, PHARMACEUTICAL COMPOSITIONS AND METHODS

[75] Inventors: Takeo Iwakuma, Ageo; Takayuki Kawaguchi, Tokyo; Toyoharu Yamashita, Kitamoto; Yasuhiko Sasaki, Urawa; Tamotu Shimazaki, Sakado, all of Japan

[73] Assignee: Tanabe Seiyaku Co., Ltd., Osaka, Japan

[21] Appl. No.: 306,867

[22] Filed: Feb. 6, 1989

[51] Int. Cl.$^5$ .................. A61K 31/215; C07C 323/07; C07C 311/19

[52] U.S. Cl. ...................... 514/539; 514/562; 514/602; 514/604; 514/618; 514/445; 560/10; 560/12; 560/13; 562/427; 562/430; 564/84; 564/92; 549/65

[58] Field of Search .............. 560/10, 12, 13; 562/427, 430; 564/84, 92; 514/539, 562, 602, 604, 445, 618

[56] References Cited

U.S. PATENT DOCUMENTS 4,258,058 3/1981 Witte et al. ....................... 560/10
4,443,477 4/1984 Witte ................................. 514/562

FOREIGN PATENT DOCUMENTS 0223593 5/1987 European Pat. Off. .
255728 2/1988 European Pat. Off. .
3610643 10/1987 Fed. Rep. of Germany .

Primary Examiner—Werren B. Lone
Assistant Examiner—Vera C. Clarke
Attorney, Agent, or Firm—Browdy and Neimark

[57] ABSTRACT

Novel phenoxyacetic acid derivative of the formula:

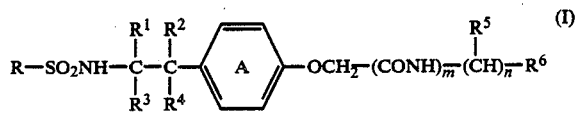

wherein R is a substituted or unsubstituted phenyl group, naphthyl group or a sulfur-containing 5-membered hetero-monocyclic group, $R^1$, $R^2$, $R^3$ and $R^4$ are hydrogen atom, a lower alkyl group, a phenyl-lower alkyl group or phenyl group, $R^5$ is hydrogen atom or a lower alkyl group, $R^6$ is carboxyl group, a protected carboxyl group, hydroxy group or a di(lower alkyl)-amino group, Ring A is a substituted or unsubstituted phenylene group, m is 0 or 1 and n is an integer 0 to 5, provided that, when m is 0,
(1) at least either one of $R^1$ to $R^4$ is or/are a phenyl-lower alkyl group or phenyl group,
(2) at least either one of $R^1$ to $R^4$ is or/are a lower alkyl group, and $R^6$ is hydroxy group, or
(3) all of $R^1$ to $R^4$ are hydrogen atom, and Ring A is a substituted phenylene group, or a pharmaceutically acceptable salt thereof are disclosed. Said derivative (I) and a pharmaceutically acceptable salt thereof have a potent platelet aggregation-inhibiting activity.

9 Claims, No Drawings

PHENOXYACETIC ACID DERIVATIVES, PHARMACEUTICAL COMPOSITIONS AND METHODS

FIELD OF THE INVENTION

This invention relates to novel phenoxyacetic acid derivatives and processes for preparation thereof.

PRIOR ART

Thromboxan $A_2$ (hereinafter, referred to as "$TxA_2$") is a metabolite of arachidonic acid which exists widely in various organs of animals (e.g. liver, kidney, lung, brain, etc.). Said $TxA_2$ is known to show platelet aggregation activity and induces a variety of thrombosis such as peripheral vascular thrombosis, pulmonary embolism, coronary artery thrombosis, myocardial infarction, transient ischemia, and the like. In this connection, 4-(2-benzenesulfonylaminoethyl)-phenoxyacetic acid which shows $TxA_2$-antagonistic activity has been suggested to be useful for therapeutic treatment of these diseases (cf. Thrombosis Research, 35, 379–395, 1984).

BRIEF DESCRIPTION OF THE INVENTION

An object of the present invention is to provide novel phenoxyacetic acid derivatives which show stronger $TxA_2$ antagonistic activity as compared with the above known compound.

Another object of the invention are to provide a pharmaceutical composition containing said novel phenoxyacetic acid derivatives. Other object of the invention is to provide processes for preparing said compounds. Further objects and advantages of the invention will be apparent to those skilled in the art from the following description.

DETAILED DESCRIPTION OF THE INVENTION

This invention relates to phenoxyacetic acid derivatives of the formula:

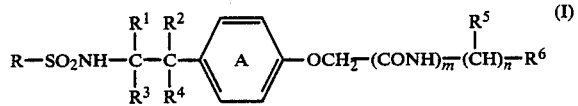

wherein R is a substituted or unsubstituted phenyl group, naphthyl group or a sulfur-containing 5-membered hetero-monocyclic group, $R^1$, $R^2$, $R^3$ and $R^4$ are hydrogen atom, a lower alkyl group, a phenyl-lower alkyl group or phenyl group, $R^5$ is hydrogen atom or a lower alkyl group, $R^6$ is carboxyl group, a protected carboxyl group, hydroxy group or a di(lower alkyl)-amino group, Ring A is a substituted or unsubstituted phenylene group, m is 0 or 1 and n is an integer of 0 to 5, provided that, when m is 0, (1) at least either one of $R^1$ to $R^4$ is or/are a phenyl-lower alkyl group or phenyl group, (2) at least either one of $R^1$ to $R^4$ is or/are a lower alkyl group, and $R^6$ is hydroxy group, or (3) all of $R^1$ to $R^4$ are hydrogen atom, and Ring A is a substituted phenylene group, or a pharmaceutically acceptable salt thereof.

Said phenoxyacetic acid derivative (I) and a pharmaceutically acceptable salt thereof show potent $TxA_2$ antagonistic and/or platelet aggregation-inhibiting activities and are useful for the therapeutic treatment, amelioration and/or prophylaxis of a variety of thrombosis or embolism, coronary and cerebral vascular smooth muscle vellication, asthma, and the like.

Examples of the phenoxyacetic acid derivatives of the invention are those of the formula (I) wherein R is phenyl group, halogenophenyl group, naphthyl group or thienyl group, $R^6$ is carboxyl group, a protected carboxyl group, hydroxy group, or di(lower alkyl)amino group and Ring A is phenylene group or a phenylene group having one to two substituent(s) selected from the group consisting of halogen atom, nitro group and amino group. A lower alkyl group, a phenyl-lower alkyl group, a lower alkoxy phenyl-lower alkyl group, a nitro phenyl-lower alkyl group, and benzhyryl group may be suitably used as the protecting group of the carboxyl group.

Among them, preferred examples of the compounds of the invention are those of the formula (I) wherein $R^1$ to $R^4$ are hydrogen atom, an alkyl group of one to four carbon atoms, benzyl group or phenyl group, $R^5$ is hydrogen atom or an alkyl group of one to four carbon atoms, $R^6$ is carboxyl group, an alkoxycarbonyl group of 2 to 5 carbon atoms, hydroxy group or a dialkylamino group of 2 to 8 carbon atoms.

Another preferred examples of the compounds of the invention are those of the formula (I) wherein R is phenyl group, chlorophenyl group or bromophenyl group, and Ring A is phenylene group or a phenylene group having one to two substituent(s) selected from the group consisting of fluorine atom and nitro group.

More preferred examples of the compounds of the invention are those of the formula (I) wherein R is chlorophenyl group, $R^1$ to $R^4$ are hydrogen atom or an alkyl group of one to four carbon atoms, $R^5$ is hydrogen atom, $R^6$ is carboxyl group and Ring A is phenylne group or a mono- or di-fluoro phenylene group.

The compounds (I) of the invention may exist in the form of two, four or eight optically active isomers due to one, two or three asymmetric carbon atom(s), and this invention includes these optically active isomers and a mixture thereof.

According to this invention, the compound (I) can be prepared by the steps of:

(A) condensing a phenol compound of the formula:

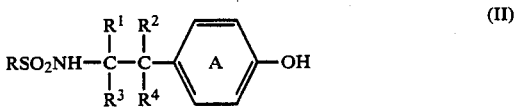

wherein the symbols are the same as defined above, or a salt thereof with a compound of the formula:

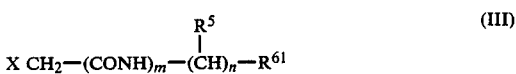

wherein $R^{61}$ is carboxyl group, a protected carboxyl group, hydroxy group, or a di(lower alkyl)amino group, X is a reactive residue and $R^5$, m, and n are the same as defined above, or a salt thereof, or (B) condensing a phenoxyacetic acid compound of the formula:

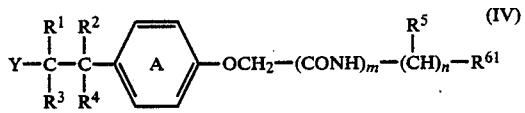

wherein Y is amino group, a protected amino group or a reactive residue and $R^1$ to $R^5$, $R^{61}$ Ring A, m and n are the same as defined above, or a salt thereof with a sulfonic acid compound of the formula:

$$RSO_2Z \qquad (V)$$

wherein Z is hydroxy group or a reactive residue when Y is amino group or a protected amino group, or Z is amino group when Y is a reactive residue, and R is the same as defined above, and, (C) if required, further removing the protecting group from the product.

The compound (I) in which Ring A is a phenylene group having a substituent selected from the group consisting of nitro group and amino group can also be prepared by nitrating a compound of the formula:

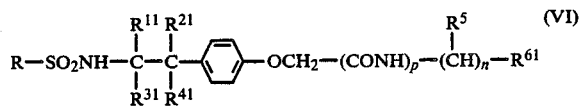

wherein R, $R^5$, $R^{61}$ and n are the same as defined above, $R^{11}$, $R^{21}$, $R^{31}$ and $R^{41}$ are hydrogen atom, a lower alkyl group, a phenyl-lower alkyl group or phenyl group and p is 0 or 1, provided that, when p is 0, (1) at least either one of $R^{11}$ to $R^{41}$ is or/are a phenyl-lower alkyl group or phenyl group, (2) at least either one of $R^{11}$ to $R^{41}$ is or/are a lower alkyl group, and $R^{61}$ is hydroxy group, or (3) all of $R^1$ to $R^4$ are hydrogen atom, and if required, further reducing the product to give the compound (I) in which Ring A is aminophenylene group, followed by optional removal of the protecting group therefrom.

On the other hand, the compound (I) in which m is 1 can also be prepared by condencing a compound of the formula:

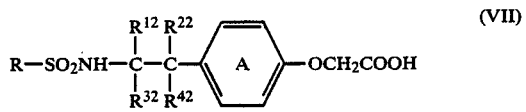

wherein $R^{12}$, $R^{22}$, $R^{32}$ and $R^{42}$ are hydrogen atom, a lower alkyl group, a phenyl-lower alkyl group or phenyl group, and R and Ring A are the same as defined above, or a reactive derivative at carboxyl group thereof with an amine compound of the formula:

wherein the symbols are the same as defined above, and if required, further removing the protecting group therefrom.

Moreover, among the compound (I), the compound of the formula:

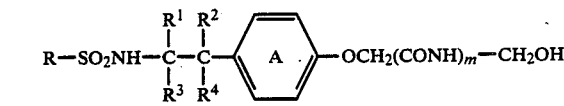

wherein the symbols are the same as defined above, can also be prepared by reducing a compound of the formula:

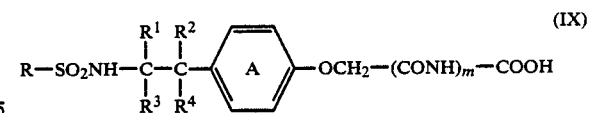

wherein the symbols are the same as defined above.

Any protecting groups which can be removed by conventional manner such as hydrolysis, acid-treatment or reduction may be used as the protecting group at carboxyl group of the starting compounds (III), (IV), (VI) and (VIII). Examples of such protecting group include a lower alkyl group, substituted or unsubstituted phenyl-lower alkyl group (benzyl group, p-methoxybenzyl group or p-nitrobenzyl group), benzhydryl group and the like. On the other hand, suitable examples of the reactive residue (X, Y or Z) include halogen atom, a lower-alkylsulfonyloxy group, benzenesulfonyloxy group, lower-alkylphenylsulfonyloxy group (e.g., p-toluenesulfonyloxy group), and the like. The starting compounds (II) to (IX) can be used in the free form or a salt thereof. Examples of the salts of the starting compounds (II), (VII) and (IX), as well as the examples of the salts of the compounds (III), (IV), (VI) and (VIII) in which $R^{61}$ is free carboxyl group, include alkali metal and alkaline earth metal salts. On the other hand, the salts of the starting compounds (IV) and (V) in which Y or Z is amino group and the salts of the amine compound (VIII) may be either inorganic or organic acid addition salts.

The condensation reaction of the phenol compound (II) and the compound (III) and the condensation reaction of the phenoxyacetic acid compound (IV) and the sulfonic acid compound (V) can be carried out in the presence or absence of an acid acceptor. The acid acceptor includes, for example, alkali metal carbonates, alkali metal bicarbonates, alkali metal hydroxides, trialkylamines, pyridine, and the like. When Y is a protected amino group, it is preferred that a lower alkanoyl group and an aryloxycarbonyl group (e.g., benzyloxycarbonyl group) are used to protect the amino group. The reaction is preferably carried out in or without a suitable solvent (e.g., acetone, alkanol, methylene chloride, tetrahydrofuran, water, ethy acetate and a mixture thereof) at a temperature of 0° to 200° C.

The nitration of the compound (VI) can be carried out by treatment with conc. nitric acid and an alkanoic acid (e.g., acetic acid), or with nitric acid and sulfric acid, in or without a solvent (e.g., acetic anhydride). The subsequent reduction can be carried out in the presence of a catalyst (e.g., palladium-carbon, palladium-black) in a solvent (alkanol, methylene chloride, tetrahydrofuran). These reactions are preferably carried out at a temperature of −10° to 50° C.

The condensation reaction of the compound (VII) or a reactive derivative thereof with the amine compound (VIII) can be carried out by any conventional method. For example, the condensation reaction of the free carboxylic acid (VII) and the compoound (VIII) can be carried out in the presence of a dehydrating agent. The dehydrating agent includes, for example, carbonyldiimidazole, dicyclohexylcarbodiimide, and the like. Besides, the condensation reaction of the reactive derivative of the compound (VII) with the compound (VIII) can be carried out in the presence or absence of an acid acceptor. A variety of the reactive derivative at the carboxyl group of the compound (VII), including, for example, acid halides (e.g., chloride, bromide), activated esters (e.g., p-nitrophenyl ester, 2,4-dinitrophenyl ester, succinimide ester, phthalimide ester) may be used for the condensation reaction. Any acid acceptors which are mentioned hereinbefore can be used in these reactions. These reactions are preferably carried out in an appropriate solvent (e.g., tetrahydrofuran, methylene chloride, ethyl acetate, alkanol, dioxane and a mixture thereof) at a temperature of 0° to 50° C.

The reduction of the compound (IX) can be carried out by treating it with a reducing agent. The reducing agent includes, for example, borane 1,4-oxathiane complex. This reduction is preferably carried out in an appropriate solvent (e.g., tetrahydrofuran) at a temperature of 0° to 50° C.

When $R^{61}$ is a protected carboxyl group and/or Y is a protected amino group, the removing of the protecting group from the product(s) obtained in the above-mentioned reaction(s) can be carried out by per se known conventional manners such as hydrolysis, solvolysis, acid-treatment or reduction.

All of the above reactions proceed without racemization, and hence, the desired compounds (I) can be obtained in an optically active form by the use of an optically active starting materials.

The compound (I) of this invention can be used for pharmaceutical use either in the form of a free base or a salt thereof. For pharmaceutical use, the salts of the compound (I) are preferably pharmaceutically acceptable salts, for example, inorganic or organic acid salts such as alkali metal salts (e.g., sodium salt, potassium salt), alkaline earth metal salts (e.g., calcium salt, magnesium salt), heavy metal salts (e.g., zinc salt), ammonium salt, organic amine salts (e.g., triethylamine salt, pyridine salt, ethanolamine salt), a basic amino acid salts (e.g., lysine salt, arginine salt or histidine salt), and the like. These salts may readily be prepared by treating the compound (I) with the corresponding inorganic or organic base in an appropriate solvent.

The compound (I) or a salt thereof may be administered either orally or parenterally to a warm-blooded animal including human beings and may also be used in the form of a pharmaceutical preparation containing the same compound in admixture with pharmaceutical excipients suitable for oral or parenteral administration. The pharmaceutical preparations may be in solid forms such as tablets, capsules and powders, or in liquid forms such as solutions, suspensions and emulsions. Moreover, when administered parenterally, it may be used in the form of injections.

As mentioned hereinbefore, the compound (I) of this invention and a salt thereof show potent $TxA_2$ antagonistic acitivity and are useful as platelet aggregation-inhibiting agent. They are also useful for the treatment, amelioration and/or prophylaxis of a variety of thrombosis or embolism, such as cerebral thrombosis, coronary artery thrombosis, pulmonary thrombosis, pulmonary embolism, peripheral vascular embolism, thromboangiitis, and the like. Moreover, the compound (I) and a salt thereof are useful for the treatment, amelioration and/or prophylaxis of myocardial ischemia, unstable angina pectoris, coronary vellication, cerebral blood vessel vellication after subarachnoid hemorrhage, cerebral hemorrhage, asthma and the like. Besides, although some known $TxA_2$ antagonists show excellent $TxA_2$ antagonistic activity but at the same time show transient $TxA_2$-like activity and hence has side effects such as platelet aggregation-inducing activity, broncho-constriction activity, blood vessel constriction activity, the compound (I) of this invention in which m is 1 does not show such $TxA_2$-like activity when administered either orally or parenterally.

Concomitantly, the starting compound (II) of the invention can be prepared by cendensing a compound of the formula:

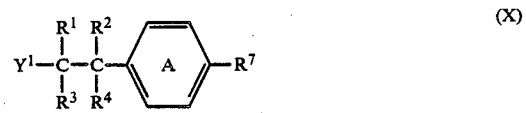

wherein $R^7$ is hydroxy group or a protected hydroxy group, $Y^1$ is amino group, a protected amino group or a reactive residue, and $R^1$ to $R^4$ and Ring A are the same as defined above, with the compound (V) in the same manner as mentioned hereinbefore.

Alternatively, the starting compound (II) in which $R^1$ is hydrogen atom and $R^2$ (or $R^4$) is a lower alkyl group or phenyl group can also be prepared by reacting the compound of the formula:

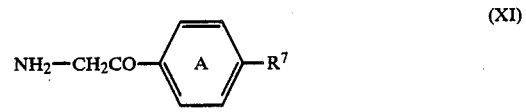

wherein $R^7$ and Ring A are the same as defined above, with the compound of the formula:

$$R-SO_2X^2 \quad (XII)$$

wherein $X^2$ is a halogen atom and R is the same as defined above, in the presence of an alkali metal carbonate in a solvent, reacting the product with a lower alkyl or phenyl magnesium halide to give a compound of the formula:

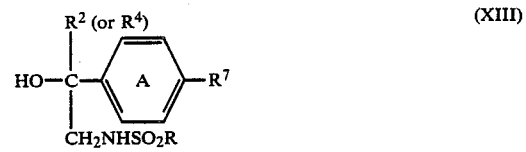

wherein the symbols are the same as defined above, subjecting the compound (XIII) to catalytic hydrogenation in the presense of palladium-carbon, and if required, further removing the protecting group therefrom.

On the other hand, the starting compound (IV) of the invention can be prepared by condensing a compound of the formula:

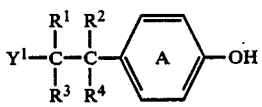

wherein the symbols are the same as defined above, with the compound (III) in the same manner as mentioned hereinbefore.

Throughout the specification and claims, the term "lower alkyl", "lower alkoxy" and "cycloalkyl" should be interpreted as referring to alkyl having one to 5 carbon atoms, alkoxy having one to 5 carbon atoms, and cycloalkyl having 3 to 6 carbon atoms, respectively.

The pharmacological activity and processes for the preparation fo the compounds of this invention are illustrated by following Experiments, Examples and Preparations.

EXPERIMENT

Inhibiting effect on arachidonic acid-induced pulmonary embolism (in vivo):

An aqueous carboxymethylcellulose (CMC) solution containing a test compound (20 ml/kg) was orally administered to ddy-male mice fasted overnight. Three hours later, arachidonic acid (125 mg/kg) was injected to the tail vein of the mice to induce pulmonary embolism, and the recovery time (minute) of locomotive activity of the mice was compared with that of a control group of mice to which a 0.25% aqueous CMC solution was administered instead of the test compound solution. The inhibiting effect of each test compound on arachiodonic acid-induced pulmonary embolism was estimated in terms of a dose (minimum effective dose) required to induce at least 15% decrease in the recovery time as compared with the control group. The results are shown in Table 1.

TABLE I

| Test Compound No. (*) (Compound of this invention) | Minimum Effective Dose (mg/kg) |
|---|---|
| 1 | 0.3 |
| 2 | 1 |
| 3 | 1 |
| 4 | 0.03 |
| 5 | 1 |
| 6 | 0.01 |
| 7 | 0.03 |
| 8 | 0.03 |
| Known compound | 30 |

(*) Chemical name of test compounds are as follows:

| Compound No. | Chemical Name |
|---|---|
| 1 | 2-(4-[2-(4-bromophenyl)sulfonylamino-1-methylethyl]phenoxy)ethanol |
| 2 | 3-(4-[2-(4-chlorophenyl)sulfonylaminopropyl]-phenoxyacetylamio)-n-propionic acid |
| 3 | 4-[2-(4-chlorophenyl)sulfonylamino-2-phenylethyl]-phenoxyacetic acid |
| 4 | 4-[2-(4-chlorophenyl)sulfonylaminoethyl]-2,6-difluorophenoxyacetic acid |
| 5 | methyl 3-[4-(2-benzenesulfonylaminoethyl)-2-fluorophenoxyacetylamino]-n-propionate |
| 6 | 3-(4-[2-(4-chlorophenyl)sulfonylaminoethyl]-2,6-difluorophenoxyacetylamino)-n-propionic acid |
| 7 | 6-(4-[2-(4-chlorophenyl)sulfonylaminoethyl]-2-fluorophenoxyacetylamino)-n-hexanoic acid |
| 8 | 2-(4-[2-(4-chlorophenyl)sulfonylaminoethyl]-2-fluorophenoxyacetylamino)-2-methylacetic acid |
| Known Compound: | 4-(2-benzenesulfonylaminoethyl)phenoxyacetic acid (a compound disclosed in Thrombosis Research, 35, 379-395, 1984) |

EXAMPLE 1

(1) 5.83 g of magnesium are suspended in 100 ml of dry tetrahydrofuran, and 5 drops of 1,2-dibromoethane are added thereto. After the mixture is stirred at room temperature, a solution of 28.3 g of phenyl iodide in 70 ml of tetrahydrofuran is added dropwise thereto. A solution of 7.65 g of 2-benzenesulfonylamino-1-(4-benzyloxyphenyl)ethanone in 100 ml of tetrahydrofuran is added dropwise to the reaction mixture under ice-cooling and stirring. The mixture is stirred at room temperature, and an aqueous ammonium chloride solution is added thereto. The mixture is extracted with ethyl acetate, and the extract is washed, dried and evaporated to remove the solvent. The residue is purified by silica gel flash column chromatography (solvent; chloroform), and recrystallized from a mixture of ethyl acetate and n-hexane. 5.37 g of 2-benzenesulfonylamino-1-(4-benzyloxyphenyl)-1-phenylethanol are obtained as colorless crystals. m.p. 147.5°–149° C.

(2) 4.91 g of the product obtained above are dissolved in a mixture of 100 ml of tetrahydrofuran and 20 ml of water, and 3.85 g of oxalic acid are added thereto. The mixture is subjected to catalytic hydrogenation in the presence of 3.2 g of 10% palladium-carbon in hydrogen gas atmosphere under the pressure of 3.5 atm at 50°–60° C. for 2.5 days. After the reaction, the catalyst is filtered off, and the filtrate is condensed to dryness. Ethyl acetate is added to the residue, and the solution is washed, dried and evaporated to remove the solvent. The residue is purified by silica gel column chromatography (solvent; chloroform:methanol=50:1) and recrystallized from a mixture of ethyl acetate, toluene and n-hexane. 3.26 g of 4-(1-phenyl-2-benzenesulfonylaminoethyl)phenol are obtained as colorless needles.

m.p. 120°–124° C.

(3) 3.10 g of the product obtained above are dissolved in 25 ml of acetone, and 1.33 g of potassium carbonate and 1.61 g of ethyl bromoacetate are added thereto. After the mixture is stirred at room temperature for 2.5 days, the solvent is distilled off, and water is added thereto. The solution is extracted with ethyl acetate, and the extract is washed, dried and evaporated to remove the solvent. The residue is purified by silica gel flash column chromatography (solvent; toluene:ethyl acetate=20:1–10:1) to give 1.85 g of ethyl 4-(1-phenyl-2-benzenesulfonylaminoethyl)phenoxyacetate as colorless oil.

liquid
IR v max (cm$^{-1}$): 3300, 1750
ms(m/e): 439 (M+)

(4) 1.81 g of the product obtained above are dissolved in 16 ml of ethanol, and 6.2 ml of 1N an aqueous sodium hydroxide solution are added thereto. After the mixture is stirred at room temperature for 2 hours, the solvent is distilled off. The residue is purified by a column packed with a non-ionic adsorption resin (manufactured by Mitsubushi Chemical Industries Ltd. under the trade mark "Diaion HP-20", hereinafter referred to as HP-20). 4 ml of 1N an aqueous sodium hydroxide solution are added to the product to give di-sodium salt. Recrystallization of the salt from isopropyl alchohol to give 1.227 g of di-sodium 4-(1-phenyl-2-benzenesulfonylaminoethyl)phenoxyacetate as colorless needles.

Yield 69%
m.p. >320° C.
Nujol
Ir ν max (cm$^{-1}$): 3440, 1620
ms(m/e): 478 (M$^+$+2Na−1), 456(M$^+$+Na), 438 (M$^+$+1)

EXAMPLE 2

(1) 6 g of 60% sodium hydride are washed with n-hexane, and 200 ml of tetrahydrofuran are added thereto. A solution of 30.7 g of diethyl malonate in 50 ml of tetrahydrofuran is added dropwise to the mixture under cooling. After the mixture is stirred at room temperature for one hour, a solution of 23.4 g of 4-benzyloxybenzyl chloride in 50 ml of tetrahydrofuran is added dropwise thereto. After the mixture is refluxed for 12 hours and cooled, 200 ml of ethanol and a solution of 22.4 g of potassium hydroxide in 100 ml of water is added thereto. After the mixture is further refluxed for 6 hours, the reaction mixture is condensed to dryness. Water is added to the residue, and the solution is extracted with ethyl acetate. The aqueous layer is made acidic with conc. hydrochloric acid and extracted with chloroform. The extract is dried and evaporated to remove the solvent. The residue is recrystallized from a mixture of ethyl acetate and n-hexane. 21.7 g of 3-(4-benzyloxyphenyl)-2-phenylpropionic acid are obtained as colorless plates.

Yield 66%
m.p. 133°–137° C.

(2) A mixture of 3.32 g of the product obtained above, 3.3 g of diphenylphosphoryl azide, 1.21 g of triethylamine and 40 ml of toluene is refluxed for 0.5 hour. 2.16 g of benzyl alchohol are added to the reaction mixture, and the mixture is refluxed for 3 hours. After the reaction, ethyl acetate is added to the reaction mixture, and the mixture is washed, dried and evaporated to remove the solvent. The residue is recrystallized from a mixture of ethyl acetate and n-hexane. 3.54 g of N-benzyloxycarboxy-2-(4-benzyloxyphenyl)-1-phenylethylamine are obtained as colorless needles.

Yield 81%
m.p. 111°–112° C.

(3) 4.37 g of the product obtained above are dissolved in a mixture of 45 ml of tetrahydrofuran and 5 ml of water, and the mixture is subjected to a catalytic hydrogenation in the presence of 450 mg of 10% palladium-carbon. 8 hours later, 250 mg of 10% palladium-carbon are added to the reaction mixture, and the mixture is stirred for 2.5 hours. The catalyst is filtered off, and 2 ml of conc. hydrochloric acid, 5 ml of water and 50 ml of ethanol are added to the filtrate. The solvent is distilled off, and the residue is recrystallized from a mixture of ethanol and ether. 2.1 g of 4-(2-amino-2-phenylethyl)-phenol hydrochloride are obtained as colorless needles.

Yield 84%
m.p. 255°–256° C.

(4) 2 g of the product obtained above are added to a mixture of 70 ml of ethyl acetate and 50 ml of a saturated aqueous sodium bicarbonate solution, and 1.69 g of 4-chlorophenylsulfonyl chloride are added thereto. After the mixture is stirred for 4 hours at room temperature, an organic layer is separated therefrom, dried and evaporated to remove the solvent. The residue is recrystallized from a mixture of ethyl acetate and n-hexane. 2.63 g of 4-[2-(4-chlorophenyl)sulfonylamino-2-phenylethyl]phenol are obtained as colorless prisms.

yield 85%
m.p. 174°–178° C.

(5) 2.52 g of the product obtained above are added to 45 ml of acetone, and 1.2 g of methyl bromoacetate and 1.8 g of potassium carbonate are added thereto. After the mixture is stirred at room temperature for 15 hours, the solvent is distilled off. Water is added to the residue, and the solution is extracted with chloroform. The extract is evaporated to remove the solvent, and the residue is dissolved in 15 ml of methanol. 5 ml of 10% an aqueous sodium hydroxide solution are added to the solution, and the mixture is allowed to stand at room temperature for 15 minutes. The reaction mixture is condensed to dryness, and the residue is dissolved in water. The solution is purified by HP-20 and recrystallized from a mixture of isopropyl alchohol, water and ether. 1.42 g of sodium 4-[2-(4-chlorophenyl)sulfonylamino-2-phenylethyl]phenoxyacetate are obtained as colorless prisms.

m.p. 215°–218° C.
Free carboxylic acid: colorless prisms.
m.p. 180°–181° C. (recrystallized from acetone and n-hexane)

EXAMPLES 3 TO 5

The corresponding starting compounds are treated in the same manner as described in Example 2-(4) and (5) to give the compounds shown in Table 2.

TABLE 2

R—SO$_2$NH—CH(R$^1$)—CH(R$^2$)—C$_6$H$_4$—OCH$_2$COOH

| Ex. Nos. | R | R$^1$ | R$^2$ | m.p. |
|---|---|---|---|---|
| 3 |  |  | H | m.p. 135–136° C. |
| 4 |  | CH$_3$ | H | m.p. 119–121° C. |
| 5 | 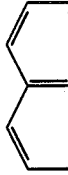 | CH$_3$ | H | m.p. 156–156.5° C. |

EXAMPLE 6

(1) 9.11 g of diisopropylamine are dissolved in 120 ml of dry tetrahydrofuran, and 54 ml of n-hexane containing n-butyl lithium (10 w/v %) are added dropwise thereto for 15 minutes at −10°–0° C. After the mixture is stirred for 10 minutes, 60 ml of tetrahydrofuran containing 12.5 g of ethyl 3-(4-methoxyphenyl)propionate are added dropwise thereto for 45 minutes at the same temperature. The mixture is stirred for 20 minutes, and 50 ml of tetrahydrofuran containing 16.4 g of benzyl bromide and 9.24 g of hexamethylphosphoric triamide are added dropwise for 10 minutes at −60° C. The mixture is stirred at the same temperature for 2 hours, warmed up to room temperature for one hour under stirring, and stirred at room temperature for an additional one hour. Then, water and 10% hydrochloric acid are added thereto under cooling. The solution is extracted with ethyl acetate, washed, dried, filtered and evaporated to remove the solvent. The residue is purified by flash column chromatography (solvent; n-hexane: ethyl acetate=30:1) to give 9.5 g of ethyl 2-benzyl-3-(4-methoxyphenyl)propionate as colorless oil.

liquid
IR $v_{max}$ (cm$^{-1}$): 1730, 1510, 1240
ms(m/e): 298 (M+)

(2) 9.49 g of the product obtained above are dissolved in 95 ml of ethanol and 42 ml of 15% an aqueous sodium hydroxide solution are added thereto. After the mixture is stirred at room temperature for one hour and refluxed for one hour, the solvent is distilled off. 20 ml of conc. hydrochloric acid are added to the residue under cooling, and the mixture is extracted with ethyl acetate. The extract is dried, filtered and evaporated to remove the solvent. The residue is recrystallized from n-hexane. 6.68 g of 2-benzyl-3-(4-methoxyphenyl)propionic acid are obtained as colorless needles.

m.p. 72°–76.5° C.

(3) 6.61 g of the product obtained above are dissolved in 75 ml of dry toluene, and 2.97 g of triethylamine and 8.08 g of diphenylphosphoryl azide are added thereto. The mixture is stirred at room temperature for 20 minutes and at 80° C. for 30 minutes, and the solvent is distilled off. 80 ml of tert-butyl alchohol are added to the residue, and the mixture is refluxed overnight. After the solvent is distilled off, the residue is dissolved in ethyl acetate, washed, dried, filtered and evaporated to remove the solvent. The residue is purified by flash column chromatography (solvent; n-hexane: ethyl acetate=10:1) and recrystallized from n-hexane. 4.83 g of tert-butyl N-(1-benzyl-4'-methoxyphenethyl)carbamate are obtained as colorless prisms.

Nujol
IR $v_{max}$ (cm$^{-1}$): 3370, 1680, 1510
ms(m/e): 342 (M+ +1)

(4) 4.68 g of the product obtained above are dissolved in 24 ml of 25% hydrogen bromide-acetic acid solution. After the mixture is dissolved, 480 ml of ether are added thereto gradually. The precipitated crystals are collected by filtration, and dried to give 3.75 g of 1-benzyl-4'-methoxyphenethylamine hydrobromide as colorless prisms.

Nujol
IR $v_{max}$ (cm$^{-1}$): 1510, 1480, 1450, 1240
ms(m/e): 242 (M+ +1)

(5) To the mixture of 4.31 g of the product obtained above, 50 ml of water, 2.48 g of sodium bicarbonate and 100 ml of ethyl acetate are added dropwise 50 ml of ethyl acetate containing 3.40 g of 4-chlorophenylsulfonyl chloride. Said dropwise addition is carried out under vigourous stirring at room temperature. The mixture is stirred for one hour. An organic layer is separated, washed, dried, filtered and evaporated to remove the solvent. 6.14 g of 2-benzyl-2-(4-chlorophenyl)sulfonylamino-1-(4-methoxyphenyl)ethane are obtained as pale yellow oil. This oil is dissolved in 90 ml of dry methylene chloride and cooled at −55°–60° C. A solution of 7.72 g of borom tribromide in 90 ml of methylene chloride is added to the mixture under argon gas atmosphere and stirring. The mixture is stirred at the same temperature for 20 minutes, and is warmed to room temperature for one hour. After the reaction, water is added to the mixture under cooling. The organic layer is separated, washhed, dried, filtered and evaporated to remove the solvent. The residue is recrystallized from a mixture of ethyl acetate and n-hexane. 4.65 g of 4-[2-benzyl-2-(4-chlorophenyl)sulfonylaminoethyl]phenol are obttained as colorless prisms.

Yield 86%
Nujol
IR $v_{max}$ (cm$^{-1}$): 3430,3280,1510,1150
ms(m/e): 401 (M+)

(6) 4.65 g of the product obtained above are treated in the same manner as described in Example 2-(5) to give 2.87 g of 4-[2-benzyl-2-(4-chlorophenyl)sulfonylaminoethyl]phenoxyacetic acid as colorless prisms.

m.p. 149.5°–151° C.

EXAMPLE 7

(1) 1 g of methyl 4-(2-aminoethyl)-2-fluorophenoxyacetate hydrochloride is added to a mixture of 30 ml of ethyl acetate, 1.58 g of potassium carbonate and 15 ml of water, and a solution of 0.78 g of 4-chlorophenylsulfonyl chloride in 15 ml of ethyl acetate is added dropwise thereto at room temperature. After the mixture is stirred for 2 hours, the ethyl acetate layer is separated therefrom, washed, dried and evaporated to remove the solvent. The residue is recrystallized from a mixture of ethyl acetate, isopropylether and n-hexane. 1.39 g of methyl 4-[2-(4-chlorophenyl)sulfonylaminoethyl]-2-fluorophenoxyacetate are obtained as colorless prisms.

m.p. 102°–103° C.

(2) 1.33 g of the product obtained above are dissolved in 10 ml of methanol, and 5 ml of an aqueous 1N sodium hydroxide solution are added thereto. After the mixture is stirred at room temperature for 30 minutes, methanol is distilled off. The residue is made acidic with 10% hydrochloric acid, extracted with ethyl acetate, dried and evaporated to remove the solvent. The residue is recrystallized from a mixture of ethyl acetate and n-hexane. 1.25 g of 4-[2-(4-chlorophenyl)sulfonylaminoethyl]-2-fluoropheoxyacetic acid are obtained as colorless prisms.

m.p. 137°–138° C.
Nujol
IR $v_{max}$ (cm$^{-1}$): 3300,1710
Sodium salt: m.p. 215°–219° C.

EXAMPLES 8 TO 10

The corresponding starting compounds are treated in the same manner as described in Example 7 to give the compounds shown in Table 3.

TABLE 3

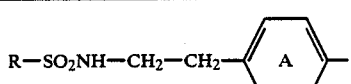

| Ex. Nos. | R | A | physical properties |
|---|---|---|---|
| 8 | 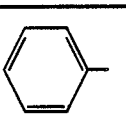 | 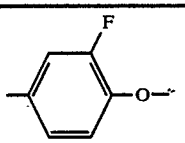 | oil IR $v_{max}^{Neat}$ (cm−1): 3290,1740 |

TABLE 3-continued

R—SO₂NH—CH₂—CH₂—A—OCH₂COOH

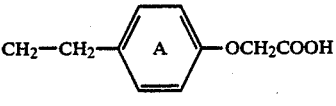

| Ex. Nos. | R | A—O— | physical properties |
|---|---|---|---|
| 9 | 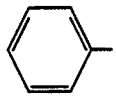 | 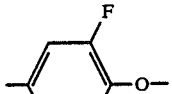 | m.p. 91–94° C. IR $\nu_{max}^{Nujol}$ (cm⁻¹): 3230,1760 |
| 10 | 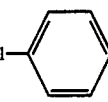 | 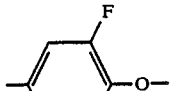 | m.p. 109–110° C. IR $\nu_{max}^{Nujol}$ (cm⁻¹): 3260,1730 Sodium salt: m.p. 283.5° C. (dec.) |

TABLE 4

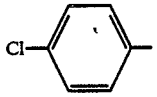

| Ex. Nos. | R | R¹ | R² | physical properties |
|---|---|---|---|---|
| 12 | 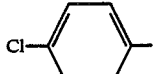 | CH₃ | H | m.p. 108.5–110.5° C. |
| 13 | 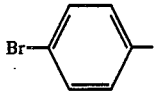 | H | CH₃ | oil IR $\nu_{max}^{liquid}$ (cm⁻¹): 3520, 3300 |
| 14 | Br—⟨ ⟩— | H | CH₃ | m.p. 105–107° C. |

EXAMPLE 11

776 mg of 4-[2-(4-chlorophenyl)sulfonylaminoethyl]-2-fluorophenoxyacetic acid are dissolved in 15 ml of tetrahydrofuran, and 1 ml of 7.8M boron-1,4-oxathiane complex is added thereto in argon gas atmosphere under ice-cooling and stirring. After the mixture is stirred at room temperature for 2 hours, 20 ml of methanol are added dropwise thereto under ice-cooling and stirring. 20 minutes later, the solvent is distilled off. The residue is purified by silica gel column chromatography [solvent; methanol-chloroform] and recrystallized from a mixture of ethyl acetate, isopropylether and n-hexane. 687 mg of 2-55 4-[2-(4-chlorophenyl)sulfonylaminoethyl]-2-fluorophenoxy} ethanol are obtained as colorless prisms.

m.p. 80.5°–82.5° C.

EXAMPLES 12 TO 14

The corresponding starting compounds are treated in the same manner as described in Example 11 to give the compounds shown in Table 4.

EXAMPLE 15

1.34 g of 4-[2-(4-chlorophenyl)sulfonylaminopropyl]-phenoxyacetic acid are dissolved in a mixture of 10 ml of methylene chloride and 10 ml of tetrahydrofuran, and 2 ml of thionyl chloride are added thereto. After the mixture is refluxed for 2 hours, the solvent is distilled off. The residue is dissolved in 10 ml of methylene chloride. The solution is added dropwise to a mixture of 312 mg of N,N-dimethyl-1,2-ethanediamine, 354 mg of triethylamine and 15 ml of methylene chloride. After the mixture is stirred at room temperature overnight, the solvent is distilled off. The residue is extracted with ethyl acetate, washed, dried and evaporated to remove the solvent. The residue is converted into oxalate thereof. The oxalate is recrystallized from a mixture of methanol, water and isopropyl alchohol. 1.47 g of 2-{4-[2-(4-chlorophenyl)sulfonylaminopropyl]phenoxyacetylamino}-N,N-dimethylethyleneamine oxalate are obtained.

Yield 77% m.p. 154°–157° C.

EXAMPLES 16 to 35

The corresponding starting compounds are treated in the same manner as described in Example 15 to give the compounds shown in Table 5.

R—SO₂NH—CH(R¹)—CH(R²)—A—OCH₂CONH—(CH₂)ₙ—COOCH₃

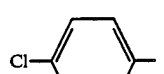

| Ex. Nos. | R | R¹ | R² | A—O— | n | physical properties |
|---|---|---|---|---|---|---|
| 16 | Cl—⟨ ⟩— | H | H | F-substituted phenoxy | 1 | (caramel) IR $\nu_{max}^{NEAT}$ (cm⁻¹):3300, 1750,1680 |

-continued
| | | | | | | |
|---|---|---|---|---|---|---|
| 17 |  | H | H | 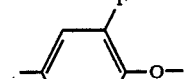 | 2 | m.p. 86–88° C. |
| 18 |  | H | H |  | 3 | m.p. 89–90.5° C. |
| 19 | 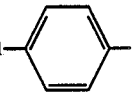 | H | H | 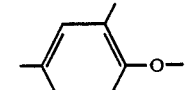 | 2 | oil<br>IR $\nu_{max}^{Neat}$ (cm$^{-1}$):3300, 1730,1670 |
| 20 | 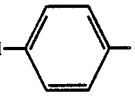 | H | H | 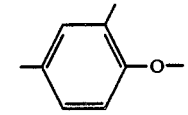 | 3 | oil<br>IR $\nu_{max}^{Neat}$ (cm$^{-1}$):3300, 1730,1670 |
| 21 | 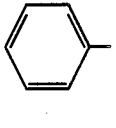 | H | H | 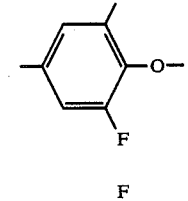 | 2 | oil<br>IR $\nu_{max}^{Neat}$ (cm$^{-1}$):3290, 1740,1670 |
| 22 | 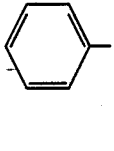 | H | H | 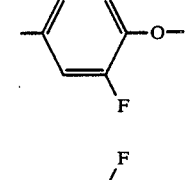 | 3 | oil<br>IR $\nu_{max}^{Neat}$ (cm$^{-1}$):3380, 3250,1710,1670 |
| 23 | 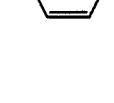 | H | H | 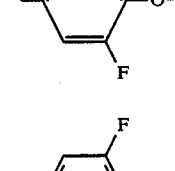 | 2 | oil<br>IR $\nu_{max}^{Neat}$ (cm$^{-1}$):3290, 1740,1670 |
| 24 |  | CH$_3$ | H |  | 2 | oil<br>IR $\nu_{max}^{Neat}$ (cm$^{-1}$):3280, 1730,1670 |
| 25 |  | CH$_3$ | H | 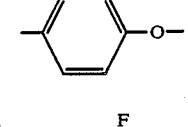 | 2 | oil<br>IR $\nu_{max}^{Neat}$ (cm$^{-1}$):1735, 1670 |
| 26 |  | H | CH$_3$ |  | 2 | m.p. 135–136° C. |

-continued

| | | | | | | |
|---|---|---|---|---|---|---|
| 27 | Cl—⌬— | H | CH₃ | F—⌬(–O—)(with F) | 2 | oil IR $\nu_{max}^{Neat}$ (cm$^{-1}$):1735,1670 |

$$R-SO_2NH-\underset{R^1}{CH}-\underset{R^2}{CH}-⌬-OCH_2CONH-(CH_2)_n-COOCH_3$$

| Ex. Nos. | R | R¹ | R² | n | physical properties |
|---|---|---|---|---|---|
| 28 | Cl—⌬— | CH₃ | H | 2 | oil IR $\nu_{max}^{liquid}$ (cm$^{-1}$):3280, 1735,1670 |
| 29 | Cl—⌬— (R-isomer) | CH₃ | H | 2 | oil IR $\nu_{max}^{liquid}$ (cm$^{-1}$):3280, 1735,1670 |
| 30 | Cl—⌬— | CH₃ | H | 3 | oil IR $\nu_{max}^{liquid}$ (cm$^{-1}$):3380, 3300,1730,1660 |
| 31 | ⌬— | ⌬— | H | 2 | m.p. 143–144° C. |
| 32 | ⌬— | H | CH₃ | 2 | oil IR $\nu_{max}^{liquid}$ (cm$^{-1}$):3300, 1730,1670 |
| 33 | Cl—⌬— | H | CH₃ | 2 | oil IR $\nu_{max}^{liquid}$ (cm$^{-1}$):3290, 1735,1670 |
| 34 | Br—⌬— | H | CH₃ | 3 | oil IR $\nu_{max}^{liquid}$ (cm$^{-1}$):3280, 1730,1660 |

$$Cl-⌬-SO_2NH-\underset{CH_3}{CH}-CH_2-⌬-OCH_2CONH-(CH_2)_2-R^4$$

| Ex. No. | R⁴ | physical properties |
|---|---|---|
| 35 | OH | m.p. 79–82° C. |

EXAMPLE 36

1.15 g 4-[2-(4-chlorophenyl)sulfonylaminopropyl]-phenoxyacetic acid are dissolved in a mixture of 7 ml of methylene chloride and 7 ml of tetrahydrofuran, and 2.2 ml of thionyl chloride are added thereto. After the mixture is refluxed for 2 hours, the solvent is distilled off to give 4-[2-(4-chlorophenyl)sulfonylaminopropyl]-phenoxyacetyl chloride as ocherous oil. The product obtained above is dissolved in 10 ml of tetrahydrofuran. The solution and 6 ml of 0.6N an aqueous sodium hydroxide solution are added dropwise to a mixture of 787 mg of 6-aminohexanoic acid, 11 ml of 0.6N an aqueous sodium hydroxide solution, 20 ml of ethanol and 10 ml of ether under stirring at the same time. After the mixture is stirred at room temperature overnight, 50 ml of water and 50 ml of ether are added thereto. The aqueous layer is made acidic with 10% hydrochloric acid, extracted with ethyl acetate, washed, dried, filtered, and evaporated to remove the solvent. Thus obtained pale yellow caramel is purified by silica gel column chromatography (solvent; chloroform, then chloroform: methanol=9:1) to give 1.50 g of 6-{4-[2-(4-chlorophenyl)sulfonylaminopropyl]phenoxyacetylamino}-n-hexanoic acid as colorless oil.

liquid
IR $\nu_{max}$ (cm$^{-1}$): 3270,1710,1660 ms(m/e): 497 (M++1)

EXAMPLES 37 TO 38

The corresponding starting compounds are treated in the same manner as described in Example 36 to give the compounds shown in Table 6.

TABLE 6

Cl—[phenyl]—SO$_2$NH—CH$_2$—CH$_2$—[phenyl(F)]—O—CH$_2$CONH—CH(R$^5$)—(CH)$_n$—COOH

| Ex. Nos. | R$^5$ | n | physical properties |
|---|---|---|---|
| 37 | H | 5 | oil<br>IR $\nu_{max}^{Neat}$ (cm$^{-1}$): 3280, 1710, 1650 |
| 38 | CH$_3$ | 1 | m.p. 174–175.5° C. |

EXAMPLE 39

623 mg of methyl {4-[2-(4-chlorophenyl)sulfonylaminoethyl]-2-fluorophenoxyacetylamino}acetate are dissolved in 8 ml of methanol, and 2.8 ml of an aqueous 1N sodium hydroxide solution are added thereto. After the mixture is allowed to stand for 3 hours, the mixture is made acidic with 10% hydrochloric acid, extracted with ethyl acetate, dried and evaporated to remove the solvent. The residue is recrystallized from a mixture of tetrahydrofuran, isoproylether and n-hexane. 560 mg of {4-[2-(4-chlorophenyl)sulfonylaminoethyl]-2-fluorophenoxyacetylamino}acetic acid are obtained as colorless prisms.

m.p. 186.5°–187.5° C.
Sodium salt: m.p. 216°–217° C.

EXAMPLES 40 TO 57

The products obtained in Examples 17 to 34 are treated in the same manner as described in Example 39 to give the compounds shown in Table 7.

TABLE 7

R—SO$_2$NH—CH(R$^1$)—CH(R$^2$)—A—OCH$_2$CONH—(CH$_2$)$_n$—COOH

| Ex. Nos. | R | R$^1$ | R$^2$ | A—O— | n | physical properties |
|---|---|---|---|---|---|---|
| 40 | phenyl | H | H | 2-F-phenyl-O— | 2 | m.p. 128.5–130° C. |
| 41 | phenyl | H | H | 2-F-phenyl-O— | 3 | m.p. 124–127° C. |
| 42 | 4-Cl-phenyl | H | H | 2-F-phenyl-O— | 2 | m.p. 114.5–115.5° C. |
| 43 | 4-Cl-phenyl | H | H | 2-F-phenyl-O— | 3 | m.p. 147.5–149° C. |
| 44 | phenyl | H | H | 2,6-diF-phenyl-O— | 2 | m.p. 119–120.5° C. |

TABLE 7-continued

| Ex. Nos. | R | R¹ | R² | Ar | n | physical properties |
|---|---|---|---|---|---|---|
| 45 | phenyl | H | H | 2,6-difluoro-4-(O—)phenyl | 3 | m.p. 104–105.5° C. |
| 46 | 4-Cl-phenyl | H | H | 2,6-difluoro-4-(O—)phenyl | 2 | m.p. 136–138° C. |
| 47 | phenyl | CH₃ | H | 2-fluoro-4-(O—)phenyl | 2 | oil<br>CHCl₃<br>IR$\nu_{max}$ (cm$^{-1}$): 3440, 3250, 1720, 1680 |
| 48 | 4-Cl-phenyl | CH₃ | H | 2-fluoro-4-(O—)phenyl | 2 | m.p. 128–129° C. |
| 49 | phenyl | H | CH₃ | 2-fluoro-4-(O—)phenyl | 2 | m.p. 136–138° C. |
| 50 | 4-Cl-phenyl | H | CH₃ | 2-fluoro-4-(O—)phenyl | 2 | m.p. 141–146° C. |

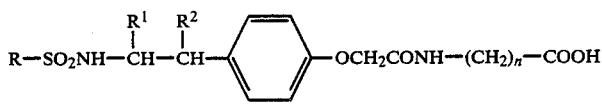

$$R-SO_2NH-\overset{R^1}{\underset{|}{CH}}-\overset{R^2}{\underset{|}{CH}}-\text{C}_6\text{H}_4-OCH_2CONH-(CH_2)_n-COOH$$

| Ex. Nos. | R | R¹ | R² | n | physical properties |
|---|---|---|---|---|---|
| 51 | 4-Cl-phenyl | CH₃ | H | 2 | m.p. 93–94° C. |
| 52 | 4-Cl-phenyl | CH₃<br>(R-isomer) | H | 2 | m.p. 129–130° C. |
| 53 | 4-Cl-phenyl | CH₃ | H | 3 | oil<br>liquid<br>IR$\nu_{max}$ (cm$^{-1}$): 3400–3200, 1710, 1660 |
| 54 | phenyl | phenyl | H | 2 | m.p. 181–183° C. |

TABLE 7-continued

| | | | | |
|---|---|---|---|---|
| 55 | phenyl | H | CH$_3$ | 2 m.p. 137–139° C. |
| 56 | 4-Cl-phenyl | H | CH$_3$ | 2 m.p. 118–120° C. |
| 57 | 4-Br-phenyl | H | CH$_3$ | 3 m.p. 115–117° C. |

EXAMPLE 58

5 g of 4-(2-benzenesulfonylaminoethyl)phenoxyacetic acid are added to 30 ml of acetic anhydride, and 3 ml of a mixture of conc. nitric acid and acetic acid (1:2) are added thereto under ice-cooling and stirring. After the mixture is reacted for 4 hours at room temperature, the mixture is poured into a mixture of diluted hydrochloric acid and ice, extracted with ethyl acetate, dried and evaporated to remove the solvent. The residue is purified by silica gel column chromatography (solvent; chloroform: ethanol=60:1) and recrystallized from a mixture of ethyl acetate and n-hexane. 3.70 g of 4-(2-benzenesulfonylaminoethyl)-2-nitrophenoxyacetic acid are obtained as colorless needles.

m.p. 135°–136° C.
Sodium salt: pale yellow needles
m.p. 93°–100° C.

EXAMPLE 59

2.18 g of sodium 4-(2-benzenesulfonylaminoethyl)-2-nitrophenoxyacetate are dissolved in 50 ml of 80% methanol, and 0.44 g of 10% palladium-carbon is added thereto. After the mixture is subjected to catalytic hydrogenation for 3 hours at room temperature under atmospheric pressure, the catalyst is filtered off. The filtrate is condensed to dryness, and the residue is recrystallized from a mixture of isopropylether and water. 1.94 g of sodium 4-(2-benzenesulfonylaminoethyl)-2-aminophenoxyacetate are obtained as pale yellow scales.

m.p. 111°–115° C. (decomp.)

[Preparation of Starting compounds]

Preparation 1

(1) After a mixture of 9.8 g of 3-fluoro-4-methoxybenzaldehyde, benzene, nitromethane, n-butylamine and acetic acid is refluxed, the reaction mixture is extracted with toluene. The extract is condensed, and the residue is recrystallized from a mixture of acetic acid and n-hexane. 10 g of α-nitro-3-fluoro-4-methoxystyrene are obtained.

(2) A solution of 10 g of the above-obtained product in tetrahydrofuran is added dropwise to a suspension of lithium aluminium hydride, and the mixture is refluxed. The reducing agent is decomposed and filtered off, and the filtrate is condensed to dryness. 15% hydrogen chloride-methanol solution is added to the residue, and the hydrochloride is recrystallized from a mixture of isopropyl alcohol and isopropylether. 6.6 g of 3-fluoro-4-methoxyphenethylamine hydrochloride are obtained.

The free amine obtained from 6.1 g of the product obtained above is dissolved in an aqueous 47% hydrogen bromide solution. After the mixture is refluxed, the solvent is distilled off. The residue is recrystallized from a mixture of isopropyl alcohol and isopropyl ether. 5.1 g of 3-fluoro-4-hydroxyphenethylamine hydrobromide are obtained.

m.p. 223.5°–226.5° C. (decomp.)

(3) 5 g of the product obtained above are dissolved in a mixture of ethyl acetate, potassium carbonate and water, and a solution of benzyloxycarbonyl chloride is added dropwise thereto under ice-cooling. After the mixture is stirred at room temperature, the organic layer is separated and evaporated to remove the solvent. The residue is recrystallized from a mixture of isopropylether and n-hexane. 5.2 g of 2-fluoro-4-benzyloxycarbonylaminoethylphenol are obtained.

m.p. 89°–90° C.

(4) 5.2 g of the product obtained above are dissolved in acetone, and potassium carbonate and methyl bromoacetate are added thereto. After the mixture is refluxed, the solvent is distilled off. The residue is extracted with ethyl acetate, washed, dried and evaporated to remove the solvent. The residue is recrystallized from a mixture of ethyl acetate, isopropyl ether and n-hexane. 6.4 g of methyl 4-benzyloxycarbonylaminoethyl-2-fluorophenoxyacetate are obtained. 5.4 g of the product are dissolved in methanol, and the mixture is subjected to catalytic hydrogenation in the presence of palladium-carbon. After the catalyt is filtered off, the filtrate is treated with hydrogen chloride in methanol and condensed. The residue is recrystallized from a mixture of methanol and ether. 3.7 g of methyl 4-(2-aminoethyl)-2-fluorophenoxyacetate hydrochloride are obtained as colorless prisms.

m.p. 126.5°–128.5° C.

Preparation 2

(1) 20 g of 4-hydroxy-3,5-difluorobenzaldehyde are dissolved in dimethylsulfoxide, and potassium carbonate and benzyl chloride are added thereto. After the mixture is stirred at room temperature, water is added thereto. The mixture is extracted with ethyl acetate and evaporated to remove the solvent. The residue is purified by silica gel column chromatography to give 17.4 g of 4-benzyloxy-3,5-difluorobenzaldehyde.

(2) The product obtained above is treated in the same manner as described in Preparation 1-(1) to (4) to give methyl 4-(2-aminoethyl)-2,6-difluorophenoxyacetate.

m.p. 222°–225° C.

Preparation 3

(1) Sodium hydride are added to tetrahydrofuran, and a solution of triethyl phosphonoacetate is added thereto in argon atmosphere. The mixture is stirred at room temperature. Then, a solution of 1.7 g of 3-fluoro-4-methoxyacetophenone in tetrahydrofuran is added thereto, and the mixture is stirred at room temperature. After the reaction, water is added to the mixture, and the organic layer is separated therefrom and evaporated to remove the solvent. The residue is purified by silica gel column chromatography to give 1.5 g of ethyl 3-(3-fluoro-4-methoxyphenyl)isocrotonate.

(2) Palladium-carbon is added to an acetic acid solution containing 1.4 g of the product obtained above, and the mixture is subjected to catalytic hydrogenation. After the reaction, the catalyst is filtered off, and the filtrate is condensed. Methanol and an aqueous sodium hydroxide solution are added to the residue, and the mixture is stirred. Then, the solvent is distilled off, and the residue is made acidic with hydrochloric acid. The aqueous mixture is extracted with ethyl acetate. The extract is condensed to dryness. The residue is purified by silica gel column chromatography, and recrystallized from n-hexane. 1 g of 3-(3-fluoro-4-methoxyphenyl)butyric acid is obtained.

(3) A solution of 1 g of the product obtained above, triethylamine and diphenylphosphorylazide in toluene is stirred at room temperature and refluxed. Benzyl alcohol are added thereto, and the mixture is again refluxed. Ethyl acetate is added to the reaction mixture, and said mixture is condensed to dryness to give 1.5 g of 1-benzyloxycarbonylamino-2-(3-fluoro-4-methoxyphenyl)propane. 25% hydrogen bromide-acetic acid solution are added dropwise to an acetic acid solution containing the product obtained above. After stirring the mixture, ether is added thereto, and the precipitated crystals are collected by filtration. 1.1 g of 1-amino-2-(3-fluoro-4-methoxyphenyl)propane hydrobromide are obtained.

(4) 1.1 g of the product obtained above and sodium bicarbonate are added to a mixture of methylene chloride and water. A solution of benzenesulfonyl chloride in methylene chloride are added dropwise to the mixture, and said mixture is stirred at room temperature. After the reaction, the methylene chloride layer is separated therefrom, and evaporated under reduced pressure. The residue is purified by silica gel column chromatography and recrystallized from a mixture of isopropylether and methanol. 1 g of 1-benzenesulfonylamino-2-(3-fluoro-4-methoxyphenyl)propane is obtained.

(5) A solution of boron tribromide in methylene chloride is added dropwise under cooling to methylene chloride containing 1 g of the product obtained above. After the mixture is stirred at room temperature, water is added thereto. The solution is extracted with chloroform and evaporated to remove the solvent. A mixture of the residue obtained, 0.7 g of methyl bromoacetate and 0.8 g of potassium carbonate are added to acetone. 0.6 g of methyl bromoacetate is further added thereto. After stirring, the mixture is evaporated under reduced pressure. Water is added the residue, and the aqueous mixture is extracted with ethyl acetate and evaporated to remove the solvent. The residue is dissolved in an aqueous sodium hydroxide solution. After the mixture is stirred, the solvent is evaporated under reduced pressure. The residue is made acidic with 10% hydrochloric acid and extracted with ethyl acetate. The extract is evaporated under reduced pressure. The residue is purified by silica gel column chromatography. 0.9 g of 2-fluoro-4-(1-methyl-2-benzenesulfonylaminoethyl)-phenoxyacetic acid are obtained.

m.p. 49°–51° C.
CHCl3
IR $v_{max}$ (cm$^{-1}$): 1740

Preparation 4

(1) A dimethoxyethane solution of 11.22 g of potassium tert-butoxide is added dropwise to a dimethoxyethane solution containing 8.40 g of 3-fluoro-4-methoxyacotophenone and 10.0 g of p-toluenesulfonylmethylisocyanide. Said dropwise addition is carried out at a temperature below −5° C. After the reaction mixture is stirred at the same temperature for 20 minutes and at room temperature for 2.5 hours, the mixture is added to ice water, and extracted with a mixture of ether and petroleum ether. The extract is washed, dried and condensed to dryness. The residue is purified by silica gel column chromatography. 4.34 g of 2-(3-fluoro-4-methoxyphenyl)-2-methylethanenitrile are obtained as colorless oil.

neat
IR $v_{max}$ (cm$^{-1}$): 2240

(2) 6 ml of Raney Nickel are added to an ethanol solution of 4.60 g of the product obtained above, and 10 g of hydrazine monohydrate are added dropwise thereto at a temperature below 50° C. After the reaction, the catalyst is filtered off, and the filtrate is evaporated. The residue is dissolved in chloroform, dried and evaporated to remove the solvent. 4.65 g of 1-amino-2-(3-fluoro-4-methoxyphenyl)propane are obtained as oil.

neat
IR $v_{max}$ (cm$^{-1}$): 3270

(3) Hydrobromic acid is added to 4.55 g of the product obtained above, and the mixture is refluxed. Then, the reaction mixture is evaporated, and the residue is crystallized with a mixture of isopropyl alcohol and isopropyl ether. 5.25 g of 4-(2-amino-1-methylethyl)-2-fluorophenol hydrobromide are obtained as colorless crystals.

m.p. 119°–121° C.

(4) 3.7 g of benzyloxycarbonyl chloride are added to a solution of 5.24 g of the product obtained above in ethyl acetate-water containing sodium bicarbonate and the mixture is stirred at room temperature for 30 minutes. After the reaction, the organic layer is separated therefrom, washed, dried and evaporated to remove the solvent. The residue is purified by silica gel column chromatography to give 6.90 g of 4-(2-benzyloxycarbonylamino-1-methylethyl)-2-fluorophenol as colorless oil.

neat
IR $v_{max}$ (cm$^{-1}$): 3350, 1700

(5) A mixture of 6.80 g of the product obtained above, 4.65 g of methyl bromoacetate, 60 ml of acetone and 4.85 g of potassium carbonate is stirred at room temperature overnight. After the reaction, the mixture is evaporated to remove acetone, and ethyl acetate and water are added to the residue. The organic layer is washed, dried, and evaporated under reduced pressure. 6.86 g of methyl 4-(2-benzyloxycarbonylamino-1-methylethyl)-2-fluorophenoxyacetate are obtained as colorless oil.

neat
IR $v_{max}$ (cm$^{-1}$): 3350, 1760, 1720

(6) 6.83 g of the product obtained above are dissolved in 100 ml of methanol and the mixture is subjected to catalytic hydrogenation in the presence of 0.7 g of 10% palladium-carbon at room temperature under atmospheric pressure. After the reaction, the catalyst is filtered off, and the filtrate is evaporated under reduced pressure. 10 ml of 17% hydrogen chloride-methanol solution are added to the residue and the solution is condensed to dryness. The residue is recrystallized from a mixture of isopropyl ether and methanol. 4.85 g of methyl 4-(2-amino-1-methylethyl)-2-fluoro-phenoxyacetate hydrochloride are obtained as colorless needles.

m.p. 135.5°–136.5° C.

(7) A mixture of 1.07 g of the product obtained above, 20 ml of ethyl acetate, 1.62 g of sodium bicarbonate, 20 ml of water and 685 mg of benzenesulfonyl chloride is stirred at room temperature for one hour. After the reaction, the organic layer is separated therefrom, washed, dried and evaporated under reduced pressure. The residue is recrystallized from a mixture of ethyl acetate and n-hexane to give 1.37 g of methyl 4-(2-benzenesulfonylamino-1-methylethyl)-2-fluorophenoxyacetate as colorless needles.

m.p. 112°–113° C.

(8) 1.32 g of the product obtained above are dissolved in 20 ml of methanol, and 7 ml of an aqueous 1N sodium hydroxide solution are added thereto. The mixture is stirred for one hour. Then, the mixture is evaporated to remove the solvent, dissolved in 10 ml of water, neutralized with 10% hydrochloric acid, and extracted with ethyl acetate. The extract is washed, dried and evaporated to remove the solvent. The residue is recrystallized from a mixture of isopropyl alcohol and water to give 1.13 g of 4-(2-benzenesulfonylamino-1-methylethyl)-2-fluorophenoxyacetic acid as colorless needles.

m.p. 49°–51° C.

Preparation 5

The corresponding starting compounds are treated in the same manner as described in Preparation 3 or 4 to give 2-fluoro-4-[1-methyl-2-(4-chlorophenyl)sulfonylaminoethyl]phenoxyacetic acid is obtained.

m.p. 106.5°–108.5° C.

Preparation 6

A tetrahydrofuran solution of 8.2 g of 1-(4-benzyloxy-3-fluorophenyl)-2-nitropropene is added dropwise to a suspension of 2.7 g of lithium alminium hydride in tetrahydrofuran. The mixture is stirred at room temperature and then refluxed. After the reaction, excess lithium alminium hydride is decomposed, and inorganic materials are filtered off. The filtrate is treated with hydrogen chloride in methanol and condensed to dryness. 6.2 g of 1-(4-benzyloxy-3-fluorophenyl)-2-aminopropane hydrochloride are obtained.

(2) 2.5 g of the product above is treated in the same manner as described in Preparation 3-(3) and (4) to give 1.8 g of 4-(2-benzenesulfonylaminopropyl)-2-fluorophenoxyacetic acid.

m.p. 148°–150° C.

Preparation 7

The corresponding starting compounds are treated in the same manner as described in Preparation 6 to give 4-[2-(4-chlorophenyl)sulfonylaminopropyl]-2-fluorophenoxyacetic acid.

m.p. 130.5°–132.5° C.

Preparation 8

(1) 78 g of 1-(4-benzyloxyphenyl)-2-chloroethanone and 63 g of hexamine are dissolved in 2.2 liters of chloroform, and the mixture is stirred at room temperature overnight. The mixture is condensed to a volume of 1.1 liters, and refluxed for 3 hours. After cooling, the precipitated crystals are collected by filtration, washed and then dried. The colorless crystals thus obtained are added to a mixture of 750 ml of ethanol and 120 ml of conc. hydrochloric acid, and the mixture is refluxed for 50 minutes. After cooling, the precipitated crystals are collected by filtration, washed and then dried. 55.6 g of 2-amino-1-(4-benzyloxyphenyl)ethanone hydrochloride are obtained as colorless crystals.

Yield 67% m.p. 225° C. (decomp.)

(2) 1.11 g of the product obtained above are dissolved in a mixture of 10 ml of tetrahydrofuran and 5 ml of water. A solution of 1.11 g of potassium carbonate in 10 ml of water and a solution of 1.41 g of benzenesulfonyl chloride in 10 ml of tetrahydrofuran are added dropwise thereto. The mixture is stirred at room temperature for 1.5 hours, and extracted with ethyl acetate. The ethyl acetate extract is washed, dried and evaporated to remove the solvent. The residue is recrystallized from ethyl acetate. 1.34 g of 2-benzenesulfonylamino-1-(4-benzyloxyphenyl)ethanone are obtained as colorless needles.

Yield 89% m.p. 148°–149° C.

(3) The product obtained above is treated in the same manner as described in Example 1 to give sodium 4-(1-methyl-2-benzenesulfonylaminoethyl)phenoxyacetate as colorless powder.

m.p. >180° C.

Free carboxylic acid: colorless caramel

CHCl3

IR $v_{max}$ (cm$^{-1}$): 1740

Preparation 9

(1) A mixture of 2.32 g of 4-(2-aminopropyl)phenol hydrobromide, 4.2 g of sodium bicarbonate, 50 ml of water, 100 ml of ethyl acetate and 2.11 g of 4-chlorophenylsulfonyl chloride is stirred at room temperature for 3 hours. After the reaction, the ethyl acetate layer is separated therefrom, dried and evaporated to remove the solvent. 3.25 g of 4-[2-(4-chlorophenyl)sulfonylaminopropyl]phenol are obtained as brown oil.

Yield 100%

CHCl3

IR $v_{max}$ (cm$^{-1}$): 3600,3380,1608

(2) 1.63 g of the product obtained above are treated in the same manner as described in Example 1-(3) to give methyl 4-[2-(4-chlorophenyl)sulfonylaminopropyl]phenoxyacetate as a crude product. The product is dissolved in 15 ml of methanol, and 4 ml of an aqueous 10% sodium hydroxide solution are added thereto. The mixture is allowed to stand at room temperature for 1 hour. Then, the mixture is made acidic with 10% hydrochloric acid, and extracted with chloroform. The extract is dried and evaporated to remove the solvent. The residue is purified by silica gel column chromatography (solvent; chloroform, and chloroform: methanol=19:1) to give 0.96 g of 4-[2-(4-chlorophenyl)sulfonylaminopropyl]phenoxyacetic acid.

m.p. 132°–136° C.

(R)-isomer: m.p. 132°–133° C.

$[\alpha]_{20}^D$ −17.33° (c = 1.027, methanol)

Preparation 10

(1) A mixture of 19.8 g of 1-amino-2-(4-methoxyphenyl)propane, 200 ml of ethyl acetate, 200 ml of water and 84 g of sodium bicarbonate is cooled at 5° to 10° C. under stirring, and 18.8 g of acetyl chloride in 100 ml of ethyl acetate are added dropwise thereto at the same temperature. After the reaction, the ethyl acetate layer is separated therefrom, washed, dried and then condensed to dryness under reduced pressure. 24.8 g of 1-acetylamino-2-(4-methoxyphenyl)propane are obtained as oil.

neat

IR $v_{max}$ (cm$^{-1}$): 3290,1650

(2) The product obtained above is dissolved in 750 ml of methylene chloride. After cooling to −60° C., a methylene chloride solution of 69 g of boron tribromide is added dropwise thereto at the same temperature for 1.5 hours under stirring. After the mixture is stirred at room temperature, said mixture is again cooled to −50°–60° C. Water and methylene chloride are added to the mixture. Then, the organic layer is separated therefrom, and washed. The aqueous layers are combined, neutralized with an aqueous sodium bicarbonate solution, and evaporated under reduced pressure. The resulting oily residue is extracted with ethyl acetate. The extract is dried, and evaporated under reduced pressure. 23.1 g of 4-(2-acetylamino-1-methylethyl)-phenol are obtained as oil.

neat

IR $v_{max}$ (cm$^{-1}$): 3290,3020,1655

(3) 23.1 g of the product obtained above are dissolved in 400 ml of acetone, and 19.9 g of methyl bromoacetate and 18 g of potassium carbonate are added thereto. The mixture is stirred overnight. 7.96 g of methyl bromoacetate and 7.2 g of potassium carbonate are further added thereto, and the mixture is stirred for 3 days. After the reaction, the mixture is evaporated under reduced pressure, and water is added to the residue. Then, the residue is extracted with ethyl acetate, washed, dried and condensed to dryness. 31.6 g of methyl 4-(2-acetylamino-1-methylethyl)phenoxyacetate are obtained as yellow oil.

Nujol

IR $v_{max}$ (cm$^{-1}$): 3310,1760,1650

(4) The product obtained above is dissolved in 200 ml of 6N hydrochloric acid, and the solution is refluxed for 7.5 hours. After the reaction, the solvent is distilled off, and the residue is crystallized with tetrahydrofuran. 19 g of 4-(2-amino-1-methylethyl)phenoxyacetic acid hydrochloride are obtained as colorless solids.

m.p. 220.5°–223° C. (decomp.)

(5) A mixture of 2.95 g of the product obtained above, 3.65 g of potassium carbonate, 30 ml of water and 2.71 g of 4-chlorophenylsulfonyl chloride is stirred at 80° C. for 2 hours. After cooling, the mixture is adjusted to pH 1 with 6N hydrochloric acid, and extracted with ethyl acetate. The extract is condensed to dryness to give 2.53 g of 4-[2-(4-chlorophenyl)sulfonylamino-1-methylethyl]phenoxyacetic acid.

m.p. 118°–119.5° C. (decomp.)

Preparation 11

The corresponding starting compound is treated in the same manner as described in Preparation 10 to give 4-[2-(4-bromophenyl)sulfonylamino-1-methylethyl]-phenoxyacetic acid.

m.p. 131°–133° C.

What is claimed is:

1. A phenoxyacetic acid derivative of the formula:

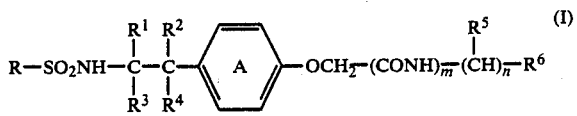

wherein R is a phenyl group, a halogenophenyl group or a naphthyl group, each of R$^1$, R$^2$, R$_3$ and R$^4$ are a hydrogen atom, an alkyl group of one to four carbon atoms, a benzyl group or a phenyl group, R$^5$ is a hydrogen atom or an alkyl group of one to four carbon atoms, R$^6$ is a carboxyl group, an alkoxycarbonyl group of two to five carbon atoms, a hydroxy group or a dialkylamino group of two to eight carbon atoms, Ring A is a phenylene group or a phenylene group having one to two substituents selected from the group consisting of halogen atoms and nitro groups, m is 0 or 1 and n is an integer of 0 to 5, provided that, when all of R$^1$ to R$^4$ are hydrogen atoms:

Ring A is a substituted phenylene group; and further provided that, when at least one of R$^1$ to R$^4$ is an alkyl group, m is 0 and R$^6$ is a carboxyl group or an alkoxycarbonyl group:

R is a naphthyl group, or a pharmaceutically acceptable salt thereof.

2. The compound claimed in claim 1, in which R is a phenyl group, chlorophenyl group or bromophenyl group, and Ring A is a phenylene group or a phenylene group having one to two substituents selected from the group consisting of fluorine atoms and nitro group.

3. The compound claimed in claim 2, the group consisting of selected from:

2-{4-[2-(4-bromophenyl)sulfonylamino-1-methylethyl]phenoxy}ethanol,

3-{4-[2-(4-chlorophenyl)sulfonylaminopropyl]-phenoxyacetylamino}-n-propionic acid, 4-[2-(4-chlorophenyl)sulfonylamino-2-phenylethyl]-phenoxyacetic acid, 4-[2-(4-chlorophenyl)sulfonylaminoethyl]-2,6-difluorophenoxyacetic acid, methyl 3-[4-(2-benzenesulfonylaminoethyl)-2-fluorophenoxyacetylamino}-n-propionate, 3-{4-[2-(4-chlorophenyl)sulfonylaminoethyl]-2,6-difluorophenoxyacetylamino}-n-propionic acid, 6-{4-[2-(4-chlorophenyl)sulfonylaminoethyl]-2-fluorophenoxyacetylamino}-n-hexanoic acid, and 2-{4-[2-(4-chlorophenyl)sulfonylaminoethyl]-2-fluorophenoxyacetylamino}-2-methylacetic acid, or a pharmaceutically acceptable salt thereof.

4. A pharmaceutical composition possessing platelet aggregation-inhibiting activity which comprises a therapeutically effective amount of a compound claimed in claim 1 and a pharmaceutically acceptable carrier therefor.

5. A pharmaceutical composition possessing platelet aggregation-inhibiting activity which comprises a therapeutically effective amount of a compound claimed in claim 2 and a pharmaceutically acceptable carrier therefor.

6. A pharmaceutical composition possessing platelet aggregation-inhibiting activity which comprises a therapeutically effective amount of a compound claimed in claim 3 and a pharmaceutically acceptable carrier therefor.

7. A method for prophylaxis or treatment of a thrombotic disease in a warm-blooded animal which comprises administering to said warm-blooded animal a therapeutically effective amount of a compound claimed in claim 1.

8. A method for prophylaxis or treatment of a thrombotic disease in a warm-blooded animal which comprises administering to said warm-blooded animal a therapeutically effective amount of a compound claimed in claim 2.

9. A method for prophylaxis or treatment of a thrombotic disease in a warm-blooded animal which comprises administering to said warm-blooded animal a therapeutically effective amount of a compound claimed in claim 3.

* * * * *